(12) United States Patent
Sauer et al.

(10) Patent No.: US 12,349,898 B2
(45) Date of Patent: Jul. 8, 2025

(54) SUTURING DEVICE STATE INDICATOR

(71) Applicant: LSI Solutions, Inc., Victor, NY (US)

(72) Inventors: Jude S. Sauer, Pittsford, NY (US);
Matthew R. Wrona, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 262 days.

(21) Appl. No.: 18/213,488

(22) Filed: Jun. 23, 2023

(65) Prior Publication Data
US 2023/0414214 A1 Dec. 28, 2023

Related U.S. Application Data

(60) Provisional application No. 63/355,924, filed on Jun. 27, 2022.

(51) Int. Cl.
*A61B 17/04* (2006.01)
*A61B 90/00* (2016.01)

(52) U.S. Cl.
CPC ... *A61B 17/0469* (2013.01); *A61B 2090/0811* (2016.02)

(58) Field of Classification Search
CPC .................. A61B 17/0469; A61B 2090/0811
See application file for complete search history.

(56) References Cited

U.S. PATENT DOCUMENTS

| 10,426,457 | B2 * | 10/2019 | Mitelberg | .......... A61B 17/0401 |
| 2018/0256159 | A1 * | 9/2018 | Sauer | .................. A61B 17/0482 |
| 2022/0362449 | A1 * | 11/2022 | Gao | ..................... A61M 39/22 |
| 2024/0206868 | A1 * | 6/2024 | Sauer | .................. A61B 17/0625 |

\* cited by examiner

*Primary Examiner* — Phong Son H Dang
(74) *Attorney, Agent, or Firm* — Michael E. Coyne

(57) ABSTRACT

A suturing device for minimally invasive surgery includes a state indicator coupled to a portion of a needle. When the needle displaces between a first needle position and a second needle position along a needle axis in a first actuation cycle, the needle rotates about the needle axis from a first rotational position to a second rotational position such that the state indicator transitions from a first visual indication to a second visual indication. When the needle displaces between the first needle position and the second needle position along the needle axis in a second actuation cycle, the needle rotates about the needle axis from the second rotational position to a third rotational position, and the state indicator transitions from the second visual indication to a third visual indication.

20 Claims, 11 Drawing Sheets

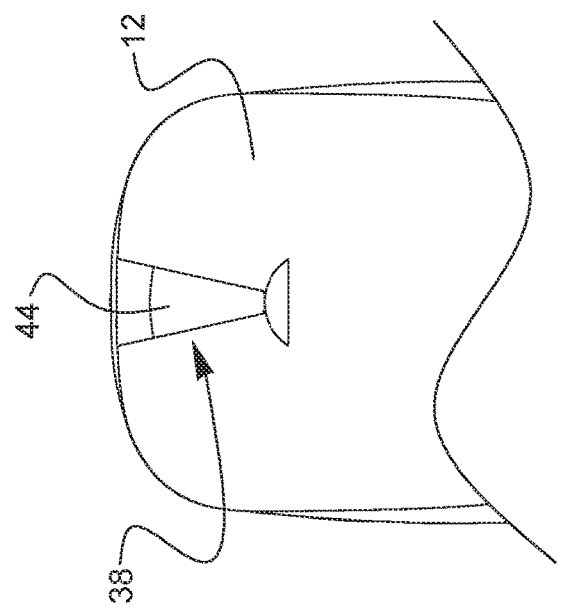
FIG. 4C
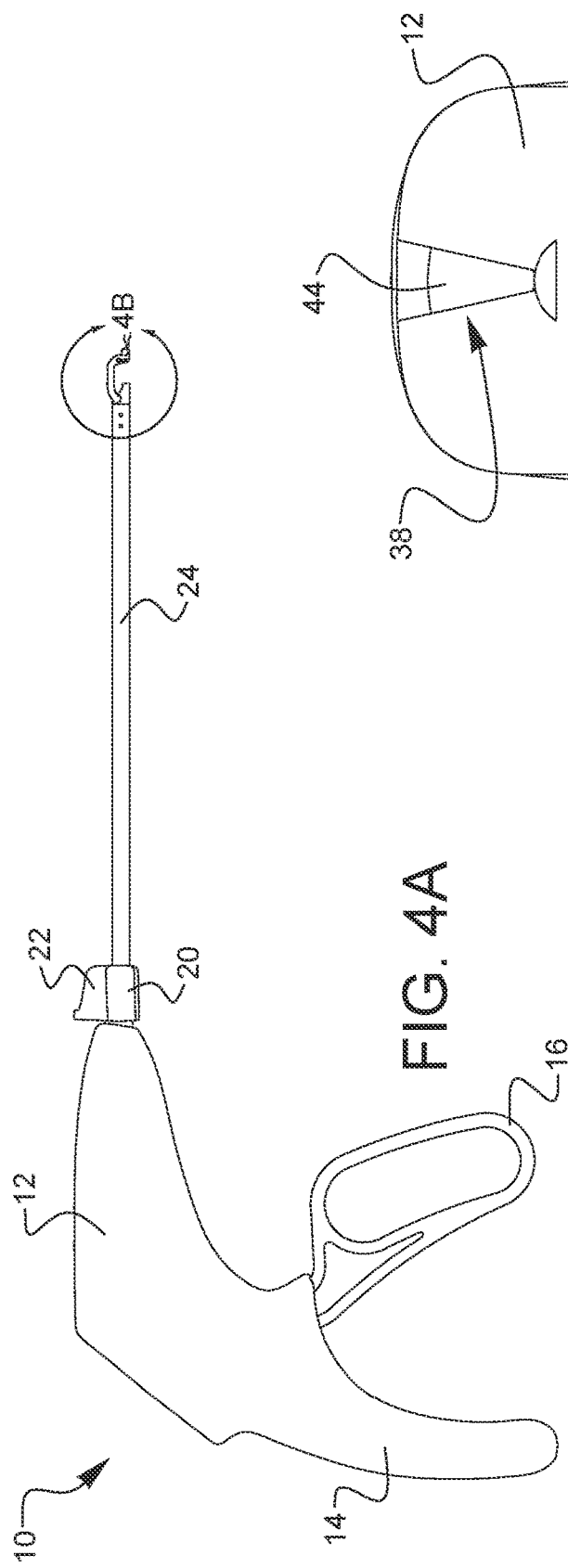
FIG. 4A
FIG. 4B

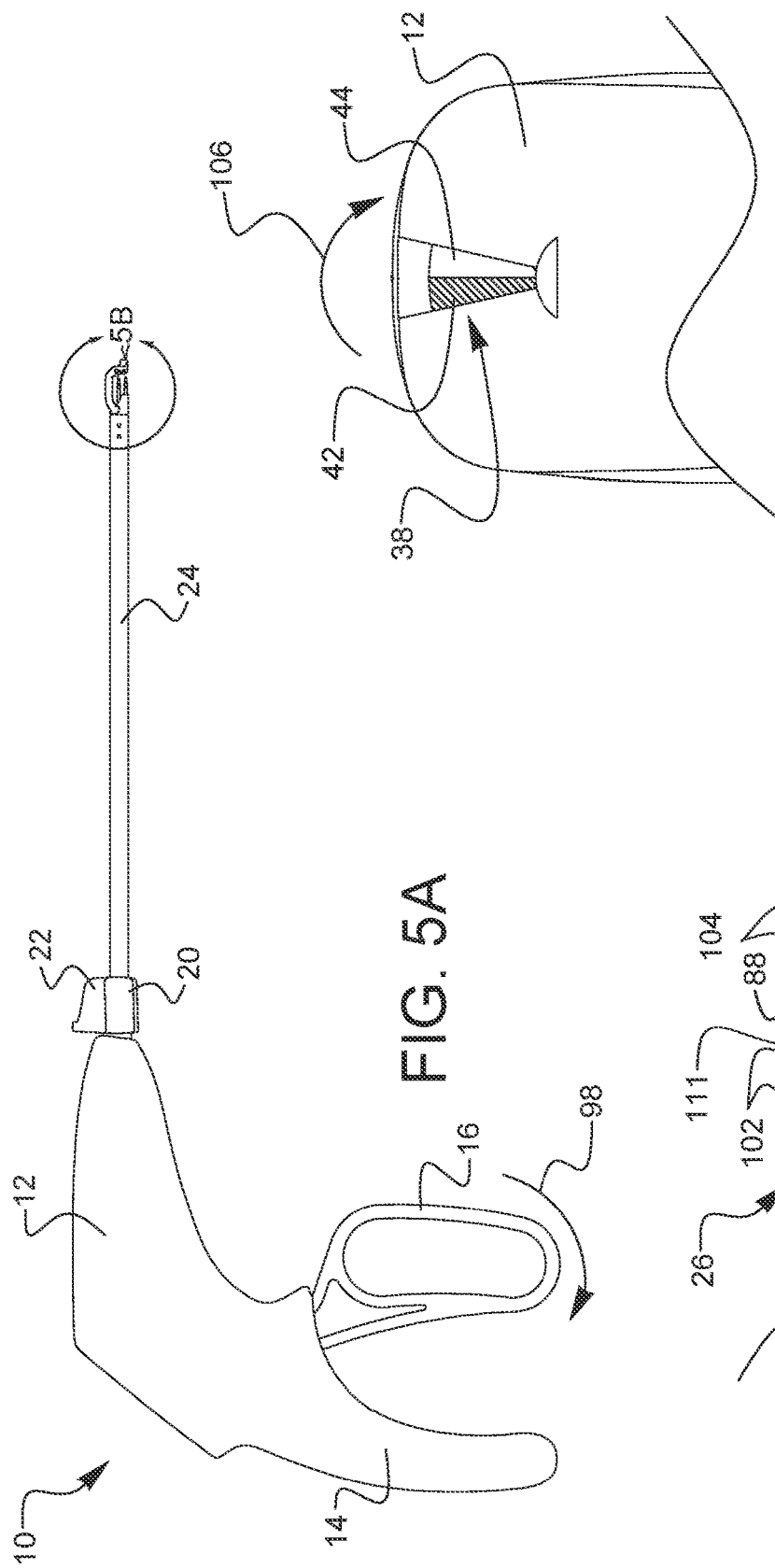
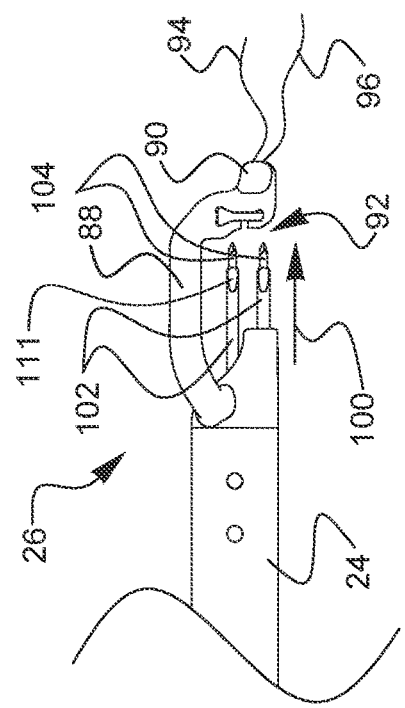
FIG. 5A
FIG. 5B
FIG. 5C

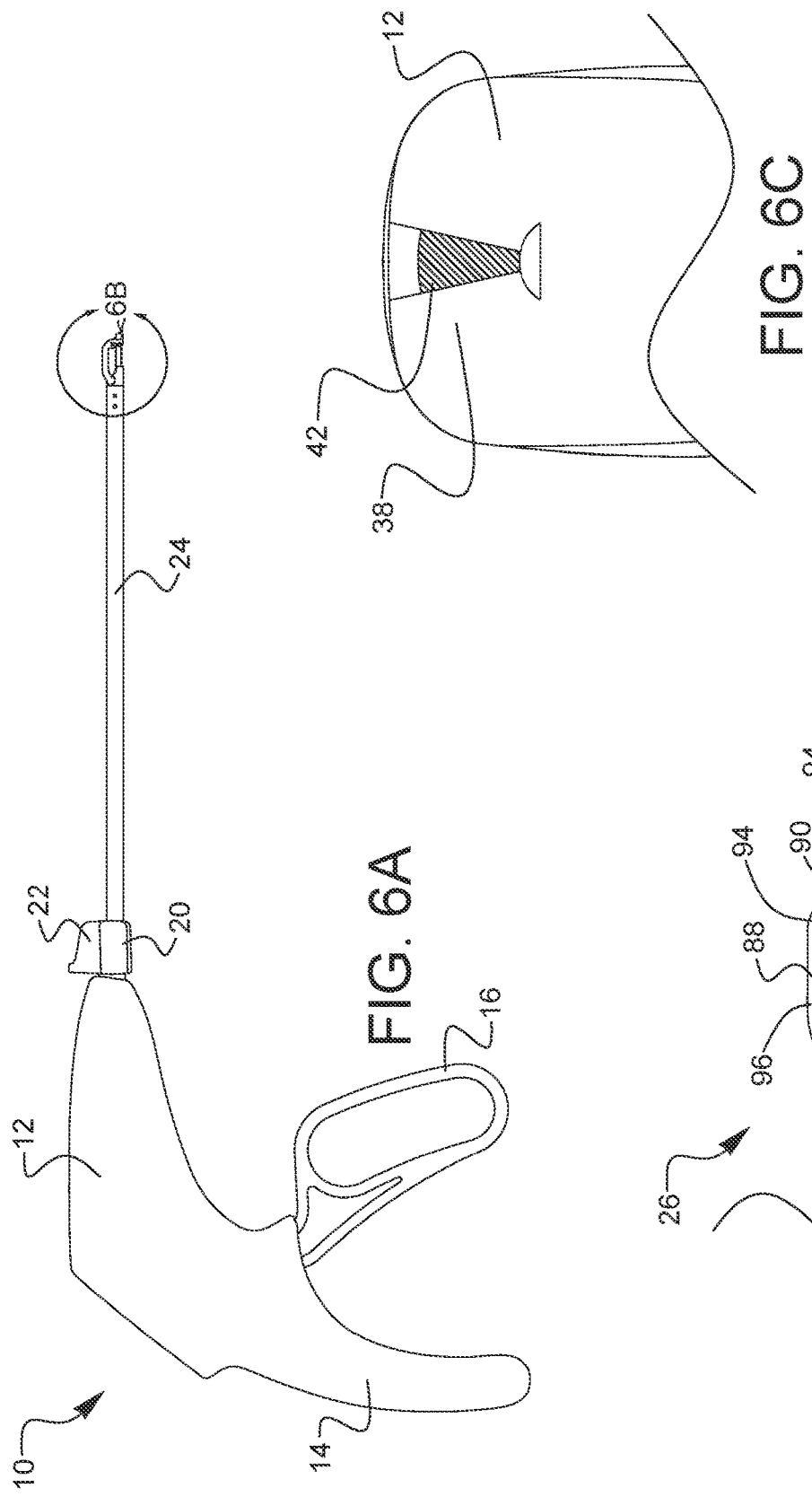

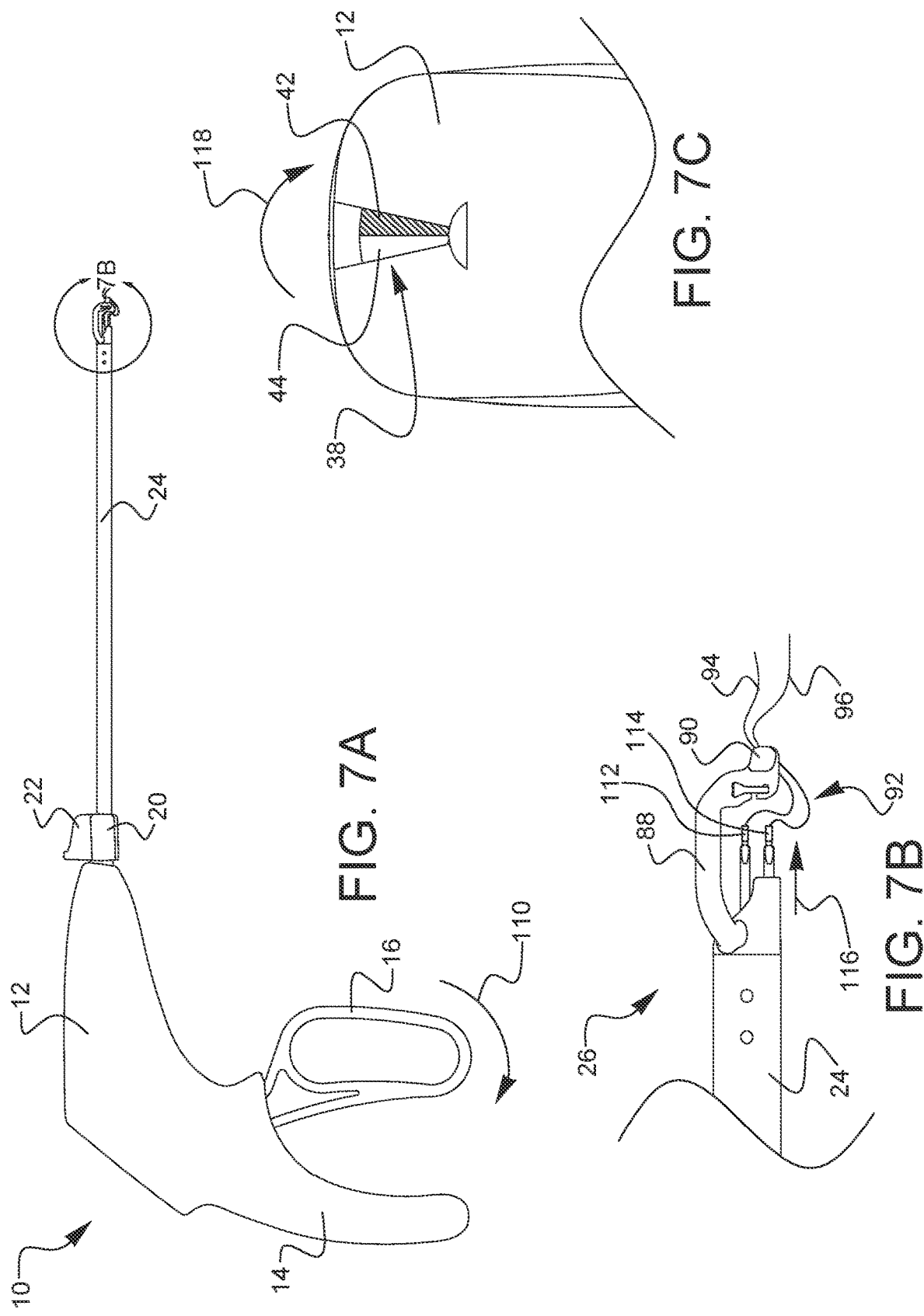

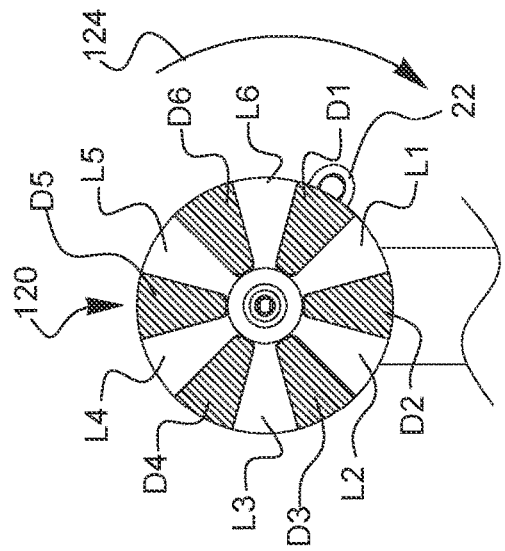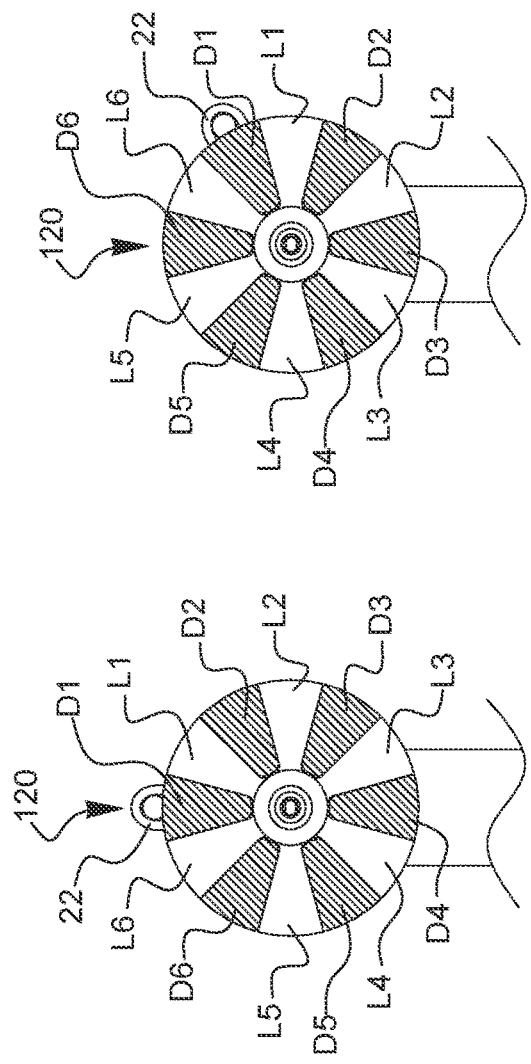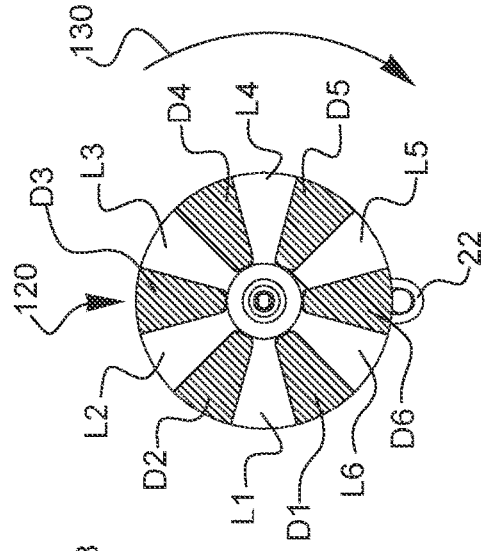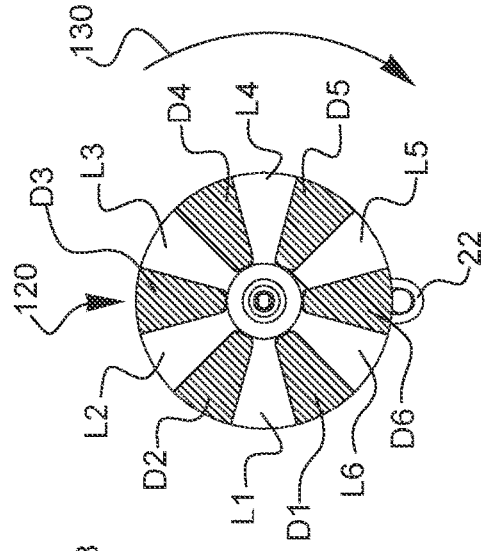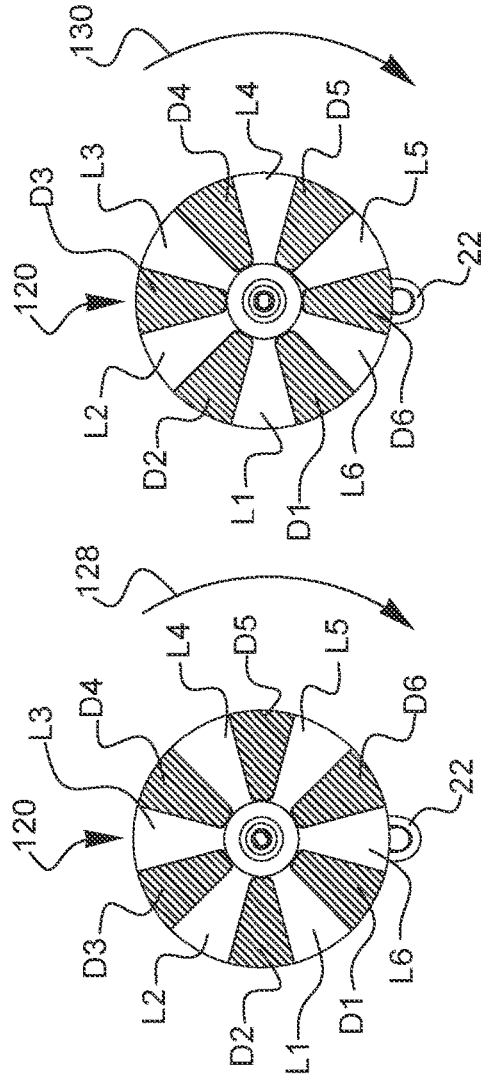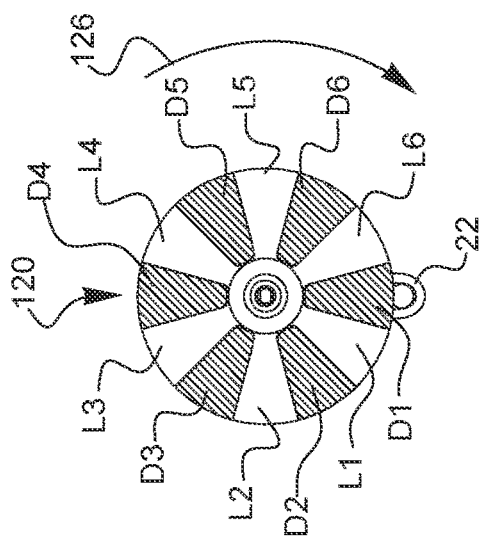

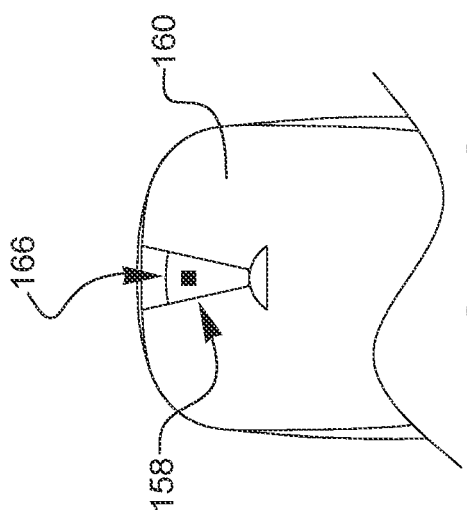
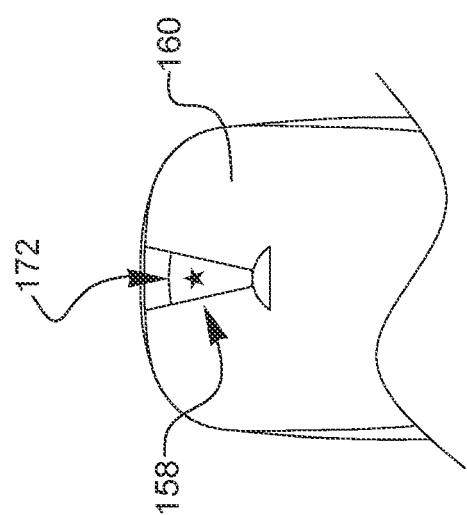
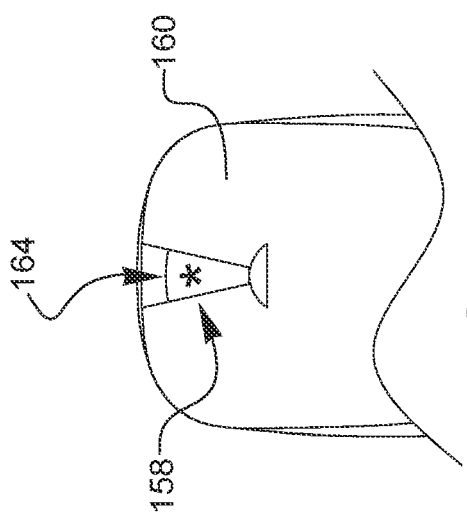
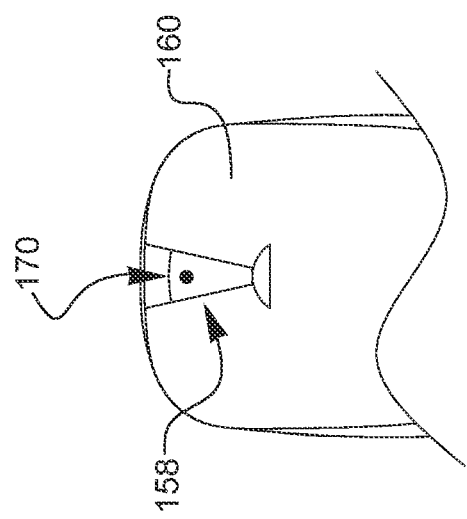
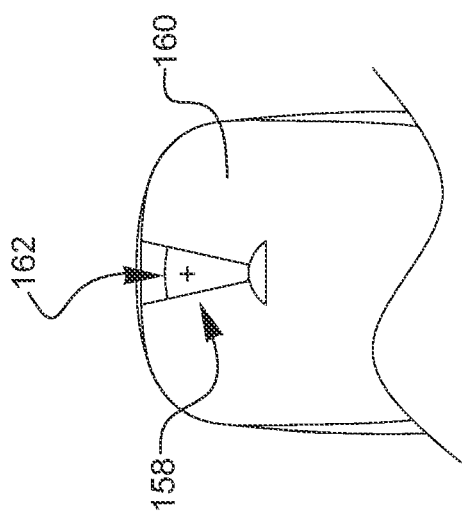
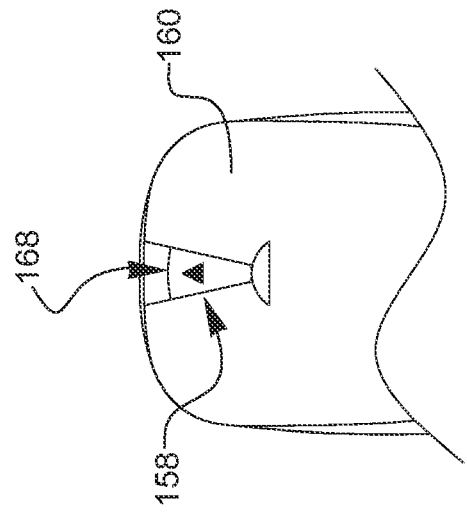

SUTURING DEVICE STATE INDICATOR

CROSS-REFERENCE TO RELATED APPLICATIONS

This application claims the benefit of U.S. Provisional Patent Application No. 63/355,924, filed Jun. 27, 2022, the contents of which is incorporated by reference herein in its entirety.

FIELD

The claimed invention relates to surgical suturing devices, and more specifically to a surgical suturing devices with device state indicators.

BACKGROUND

The human heart relies on a series of one-way valves to help control the flow of blood through the chambers of the heart. Deoxygenated blood returns to the heart, via the superior vena cava and the inferior vena cava, entering the right atrium. The heart muscle tissue contracts in a rhythmic, coordinated heartbeat, first with an atrial contraction which aids blood in the right atrium to pass through the tricuspid valve and into the right ventricle. Following atrial contraction, ventricular contraction occurs and the tricuspid valve closes. Ventricular contraction is stronger than atrial contraction, assisting blood flow through the pulmonic valve, out of the heart via the pulmonary artery, and to the lungs for oxygenation. Following the ventricular contraction, the pulmonic valve closes, preventing the backwards flow of blood from the pulmonary artery into the heart.

Oxygenated blood returns to the heart, via the pulmonary veins, entering the left atrium. Left atrial contraction assists blood in the left atrium to pass through the mitral valve and into the left ventricle. Following the atrial contraction, ensuing ventricular contraction causes mitral valve closure, and pushes oxygenated blood from the left ventricle through the aortic valve and into the aorta where it then circulates throughout the body. Under nominal conditions, prolapse of the mitral valve is prevented during ventricular contraction by chordae attached between the mitral valve leaflets and papillary muscles located in the left ventricle. Following left ventricular contraction, the aortic valve closes, preventing the backwards flow of blood from the aorta into the heart.

Unfortunately, one or more of a person's heart valves can have or develop problems which adversely affect the valves' function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve fails to properly close during a ventricular contraction. Mitral regurgitation can be caused by chordae stretching, tearing, or rupturing, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation. Several surgical instruments are well known in the art that provide a surgeon with the ability to execute a running stitch during such a procedure. One manner in which a running stitch operation is through the use of an automated suturing device wherein the needle picks up and releases ferrules or needle caps fastened to the end of suture. On occasion, disruptions or interruptions during such a surgical procedure may occur, requiring that attending surgical staff must resume precisely where they left off in a procedure. It may be desirable for a surgeon to maintain continuous awareness of the mode—ready to stitch or ready to reset, for example—a surgical suturing device is in even without interruptions.

Unfortunately, while the above techniques are proven methods of heart valve repair, technical challenges impede their widespread utilization, especially in minimally invasive cardiac surgery. While minimally invasive surgery can dramatically reduce patient recovery times by avoiding the need for full or partial sternotomy, it is difficult and time consuming to manipulate a suture needle with forceps through a minimally invasive opening between adjacent ribs to place the sutures for neochordal replacement. An innovative system that remotely delivers and reliably places suture for minimally invasive neochordal replacement would be highly desirable. It is further desirable to utilize a system or device that provides visual or other feedback to a surgeon related to the present mode of a device such that a surgical assistant or device operator can receive instantaneous feedback.

BRIEF DESCRIPTION OF THE DRAWINGS

FIGS. 4A-4C are side, enlarged and proximal views, respectively, of the surgical suturing device of FIG. 1, shown in a ready to stitch or initial state.

FIGS. 5A-5C are side, enlarged and proximal views, respectively, of the surgical suturing device of FIG. 1, shown in a partially actuated state, transitioning to a ready to reset state.

FIGS. 6A-6C are side, enlarged and proximal views, respectively, of the surgical suturing device of FIG. 1, shown in a ready to reset state.

FIGS. 7A-7C are side, enlarged and proximal views, respectively, of the surgical suturing device of FIG. 1, shown in a partially actuated state, transitioning to a ready to stitch or initial state.

FIGS. 8A-8F are a series of proximal schematic views of a suturing device indicator of the suturing device of FIG. 1.

FIGS. 11A-11F are a series of proximal schematic views of portions of alternate embodiments of surgical suturing devices.

Figure 1:
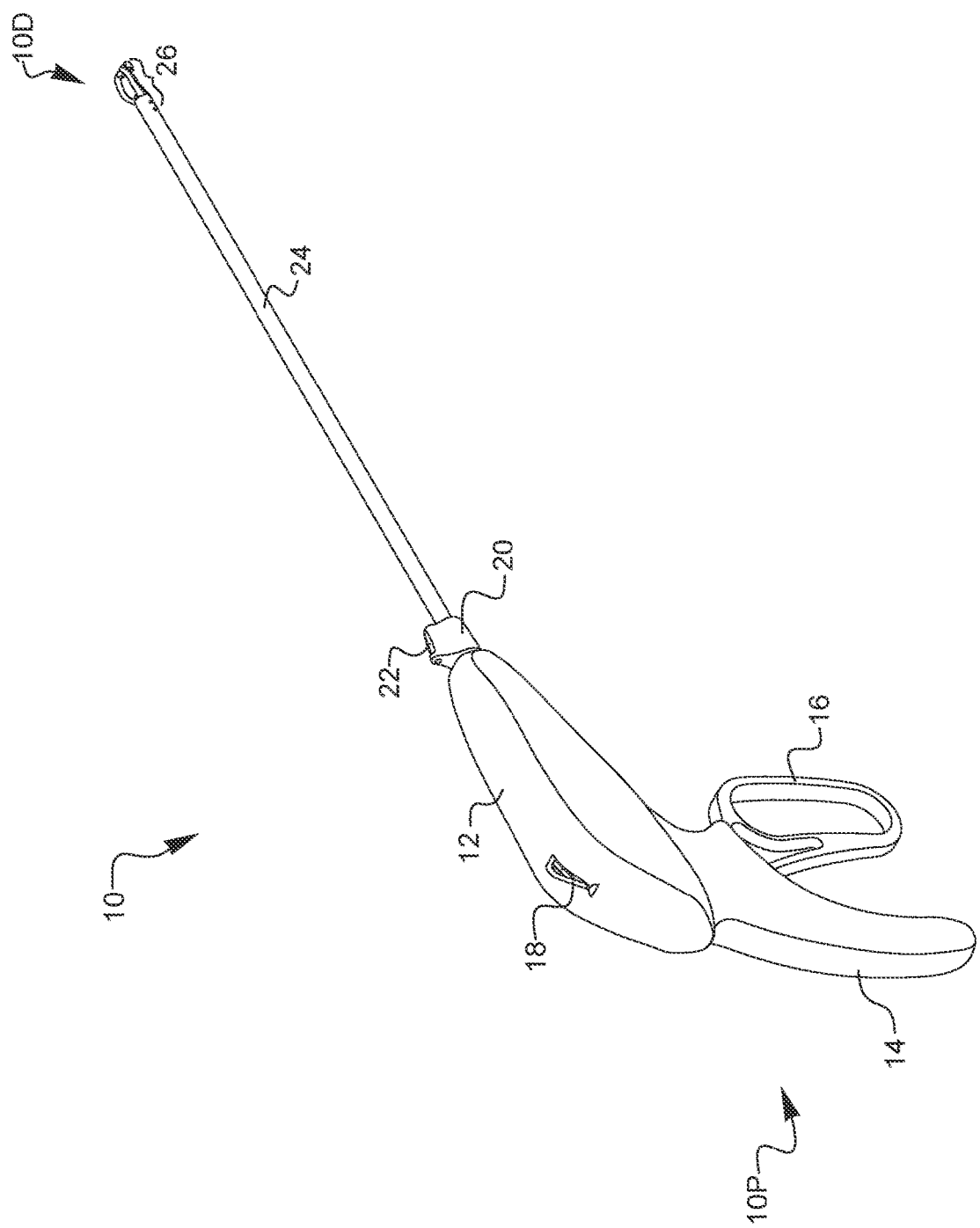
FIG. 1 is a top right proximal perspective view of a surgical suturing device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of a surgical suturing device 10 having a housing 12 that includes a portion that defines a handle 14 and a portion that includes an indicator window 18 that is disposed at or adjacent to a proximal end 10P of the surgical suturing device 10. An actuator, such as an actuation lever 16, may be movably coupled to a portion of the housing 12. A shaft 24 may be coupled to a further portion of the housing 12, and the shaft 24 may extend along a shaft axis from a proximal end to a distal end, and a tip assembly 26 may be coupled to the distal end of the shaft 24. The tip assembly 26 of the surgical suturing device 10, along with a needle tip 104 (see FIG. 5B), may be configured to suture tissue during minimally invasive surgical procedures and will be described in further detail in a following section. In the present embodiment of the illustrated surgical suturing device 10, the actuation lever 16 may be squeezed by an operator to initiate a first actuation cycle that advances a needle 60 distally such that the needle tip 104 extends through tissue disposed within a tissue bite area 92 (see FIG. 5B) defined by a portion of the tip assembly 26. The needle tip 104 may also be configured to engage (e.g., attach to be removably secured to) a ferrule 112, 114 (see FIG. 7B) that is itself releasably secured by a securing portion (e.g., a ferrule holder 90 of FIG. 7B) of the tip assembly 26 that is at or adjacent to a distal end of tissue bite area 92, and the ferrule 112, 114 may be secured to a portion of suture 94, 96. The actuation lever 16 may then be released to retract the needle 60 proximally to draw the ferrule 112, 114 and the attached portion of suture 94, 96 through the tissue to complete the first actuation cycle. A second actuation of the actuation lever 16 will result in a second actuation cycle which will again advance the needle 60 distally, at which point the ferrule 112, 114 will be stripped from the needle tip 104 and retained within the securing portion of the tip assembly 26. Examples of the engagement of the ferrule 112, 114 with the needle tip 104 and the subsequent stripping of the ferrule 112, 114 is provided in U.S. Pat. No. 7,407,505, issued on Aug. 5, 2008, and U.S. Pat. No. 10,603,031, issued on Mar. 31, 2020, the contents of each of which is hereby incorporated by reference in its entirety.

To facilitate more targeted suturing through tissue in a minimally invasive surgical site, a rotation adapter 20 may be coupled to a portion of the housing 12, and a portion of the shaft 24 may be coupled to the rotation adapter 20 to allow the shaft 24 to rotate about the shaft axis. Because the tip assembly 26 is fixedly coupled to the distal end of the shaft 24, the shaft 24 can be rotated about the shaft axis to more accurately position the tip assembly 26 during a procedure. The rotation adapter 20 may also include an indicator fin 22 that provides visual feedback to the operator regarding the direction of the tip assembly 26. In this embodiment, the tissue bite area 92 (see FIG. 5B) of the tip assembly 26 of the surgical suturing device 10 is facing in an opposite direction relative to the indicator fin 22. Other embodiments may have alternate geometrical relationships between the indicator fin 22 and the tissue bite area 92. The indicator window 18 on the housing 12 in this embodiment of a surgical suturing device 10 shown in FIG. 1 provides further feedback to the operator regarding the current step, mode or actuation cycle of the surgical suturing device 10. In this embodiment, the visual feedback in the indicator window 18 allows the user to visualize whether the device has just completed the first squeeze of the actuation lever 16 (corresponding to the first actuation cycle) or the second squeeze of the actuation lever 16 (corresponding to the second actuation cycle) as described previously. A further feature of the visual feedback provided by the surgical suturing device as described is that the visual feedback is independent of which rotational position the rotation adapter 20 is in during operation of the surgical suturing device 10. Alternate embodiments of surgical suturing devices may have different arrangements or provide visual feedback or indication of different modes or states of operation a device may be in when feedback is accessed.

Figure 3:
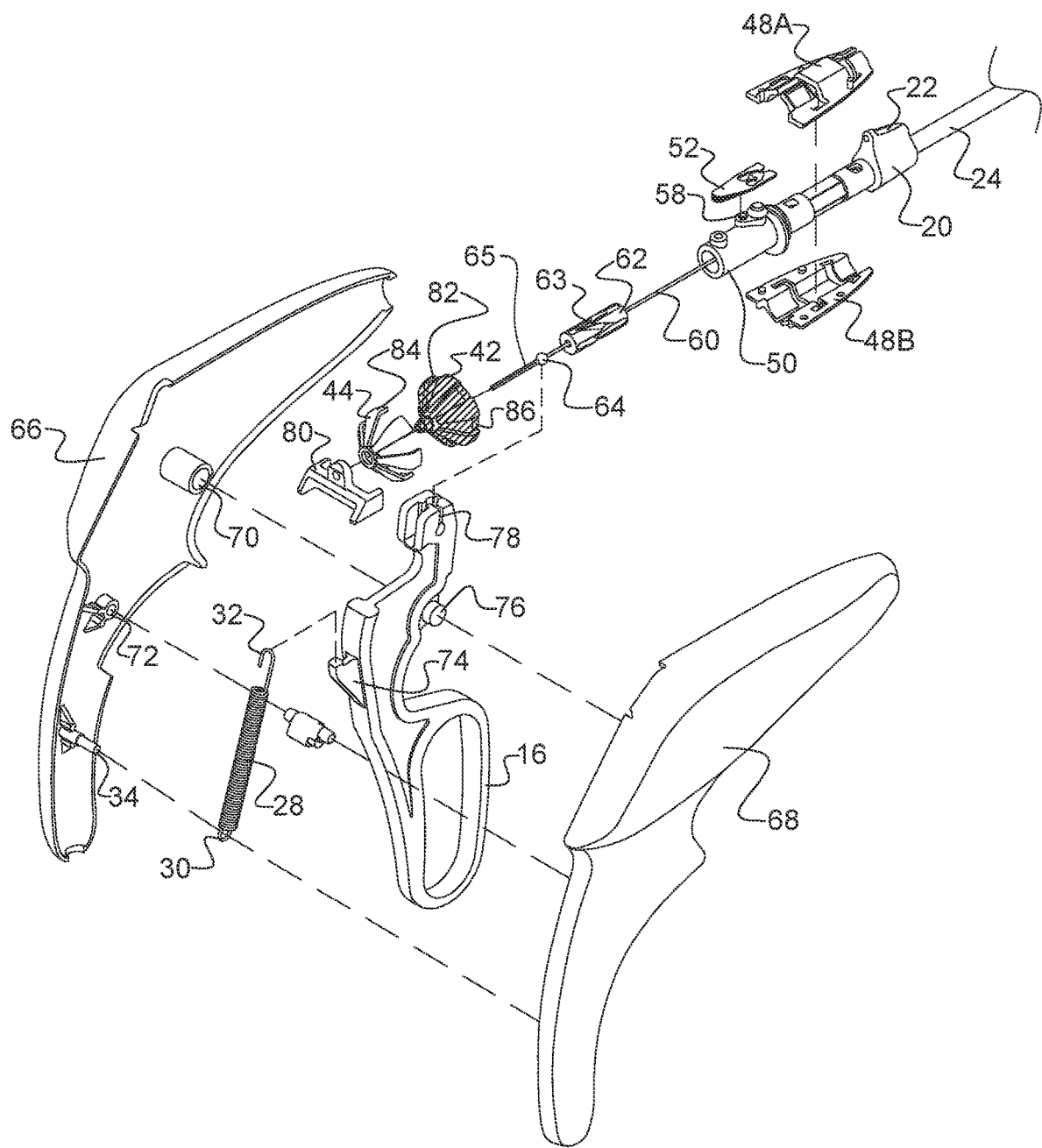
FIG. 3 is an exploded view of a portion of the surgical suturing device of FIG. 1.

The actuation lever 16 may be pivotably mounted within the housing 12. In particular, as illustrated in FIG. 3, which is an exploded view of a portion of the surgical suturing device of FIG. 1, a housing half 66 of the housing 12 includes a first boss 70 that, along with an opposing second boss (not shown) on the second housing half 68, engages a pivot portion 76 of the actuation lever 16 to allow the actuation lever 16 to pivot relative to the housing 12. The actuation lever 16 may be pivotably displaceable between a first actuator position (illustrated in FIG. 1) and a second actuator position (not shown) in which the actuation lever 16 is squeezed by a user towards the handle 14. FIG. 5A illustrates the actuation lever 16 being squeezed or pivoted towards the handle 14 in an inward direction 98 and is illustrated in an intermediate position between the first actuator position and the second actuator position, but continued rotation in inward direction 89 would result in the actuation lever 16 being in the second actuator position. The actuation lever 16 may be biased in the first actuator position by a spring 28. The spring 28 is attached with a spring hook 32 to a lever spring hook 36 on the actuation lever 16 at one end, and a spring loop 30 of the spring 28 attached to a spring mount 34 within the handle 14 portion of the housing 12 on the opposite end.

Figure 2:
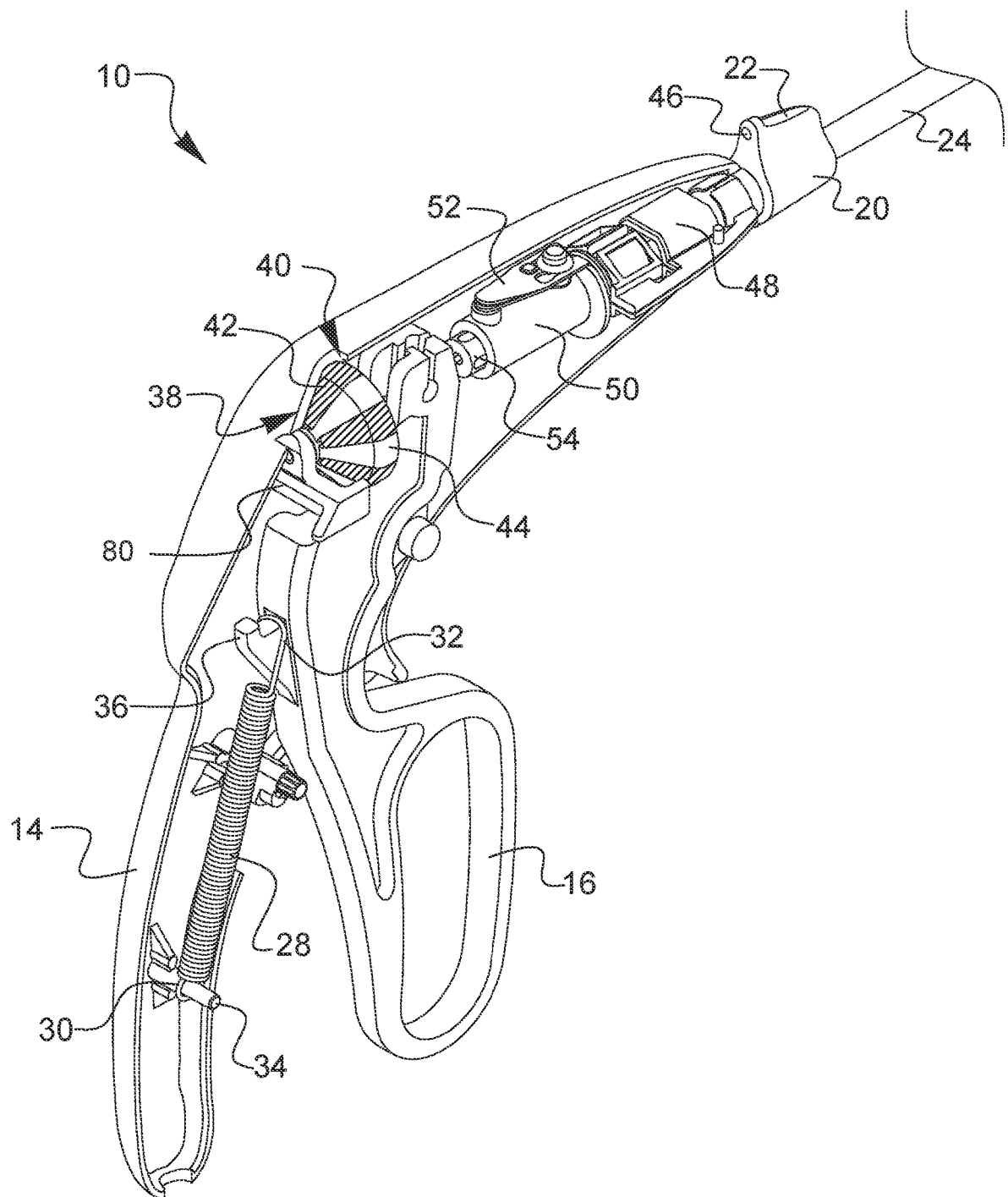
FIG. 2 is a partial cross-sectional perspective view of the surgical suturing device of FIG. 1.

Referring to FIG. 2, a bracket, such as an indicator spacer 80, may be disposed within the housing 12 adjacent to an indicator window portion 38, and the indicator spacer 80 may secure a portion of a state indicator 40 captive within the housing 12 and allow the state indicator 40 to rotate relative to the housing 12. A rotation adapter receiver 48, which may be an assembly of a top portion 48A and a bottom portion 48B (as illustrated in FIG. 3) may be coupled to a portion of the housing 12. The rotation adapter receiver 48 may surround an actuator input 50, which may be a portion of (or may be coupled to) the rotation adapter 20. A portion of the actuator input 50 may have a polygonal shape with two or more facets that are configured to correspond to facets formed in a corresponding portion of the rotation adapter receiver 48, thereby allowing the rotation adapter 20, and the shaft 24 coupled to the rotation adapter 20, to "index" into predefined rotational increments as the shaft 24 rotates about the shaft axis. These predefined rotational increments may correspond to the "flats" or facets of the polygonal shape of the portion of the actuator input 50. In the example of FIG. 3, six rotational increments (of 60 degree rotational increments) are provided, but any number of rotational increments may be contemplated. A cam spring 52 may be secured to a portion of the actuator input 50, and this cantilevered cam spring 52 may bias a cam pin 58 towards a cam barrel 62 that is disposed within a central bore of the actuator input 50. The cam barrel 62 is coupled (e.g., fixedly coupled) to a portion of the needle 60 such that a rotation of the cam barrel 62 about the longitudinal axis of the needle, or the needle axis, results in a corresponding rotation of the needle 60 about the needle axis. The cam barrel 62 includes a plurality of cam paths 63, and each cam path 63 is a groove or channel disposed along the circumferential surface of the cam barrel 62. An end portion of the cam pin 58 may be disposed in one of the cam paths 63, and when the needle 60 is displaced along the needle axis (such as when the actuator lever 16 is displaced from the first actuator position to the second actuator position, or vice versa) the engagement of the cam pin 58 with a corresponding cam path 63 of the cam barrel 62 causes the cam barrel 62 (and needle 60) to rotate along the needle axis relative to the actuator input 50.

The needle 60 may extend along the needle axis from a proximal end to a distal end, and the distal end of the needle 60 may include the needle tip 104 (see FIG. 5B) that may be configured to penetrate tissue to be sutured. The needle 60 may be a single, unitary part or may be an assembly of two or more parts or portions, with one or more of the portions having differing cross-sectional shapes and/or materials and/or material properties. As previously explained, a portion of the needle 60 is passed through the cam barrel 62 such that the proximal end of the needle 60 protrudes out a proximal end of the cam barrel 62. A ball coupler 64 may be secured to the needle distal to the proximal end of the needle 60, and the ball coupler 64 may be disposed within the ball receiver 78 of actuation lever 16 such that when the actuation lever 16 is squeezed from the first actuator position to the second actuator position and released, the displacement of the actuation lever 16 also moves the needle 60 distally and proximally, respectively.

A keyed extension 65, which may be a portion of the needle 60 or may be coupled to the needle 60, may have a first portion adjacent to the ball coupler 64, and a second portion of the keyed extension 65 (e.g., the proximal end of the needle 60) may be coupled to the state indicator 40. The state indicator 40 may have the shape of a disc, such as a conical disc, and may have a central aperture that receives the portion of the needle 60. The state indicator 40 may be a two-piece assembly of a first segment 42 (for example, a dark segment) and a second segment 44 (for example, a light segment) that may be coupled to the first segment 42. The first segment 42 and second segment 44 may cooperate to form two or more first indicia 82, such as a dark colored portion, and two or more second indicia 84, such as lighter colored portion, and the second indicia 84 of state indicator 40 may be nested within several recesses 86 on the first indicia 82 of the state indicator 40. While in this embodiment, the state indicator 40 is made from two segments 42, 44 other embodiments may be made from a single component or more than two components depending on the overall configuration of the surgical suturing device 10.

As previously explained, at least one of the one or more cam paths 63 of the rotating barrel 62 are engaged by the cam pin 58, and as the actuator lever 16 is released, the engagement of the cam pin 58 with the curved cam paths on the cam barrel 62 cause the needle 60 to rotate ninety degrees from a first rotational position to a second rotational position while the needle 60 moves in a proximal direction. Alternatively, as the actuator lever 16 is squeezed, the engagement of the cam pin 58 with the curved cam paths on the cam barrel 62 cause the needle to rotate ninety degrees from a first rotational position to a second rotational position while the needle 60 moves in a distal direction. This rotation will effectively align the needle 60 in a first position in which the needle 60 is advanced distally such that the ferrule 112, 114 secured in the ferrule holder 90 of the tip assembly 26 is engaged by the needle tip 104 and retained on the needle tip 104 as the needle 60 moves proximally (i.e., from the second needle position to the first needle position) as the actuation lever 16 is released to complete the first actuation cycle. A subsequent squeeze of the actuation lever 16 for a second actuation cycle will again cause the needle 60 to move in a distal direction (i.e., from the second needle position to the first needle position), causing the needle 60 to rotate ninety degrees from the second rotational position to a third rotational position such that when the needle 60 is displaced distally, the ferrule 112, 114 secured to the needle tip 104 is engaged by a needle stripper device (not shown), and the ferrule 112, 114 is stripped from the needle tip 104 and retained in the ferrule holder 90 of the tip assembly 26 as the needle 60 is displaced proximally as the actuation lever 16 is released. A further squeeze of the actuation lever 16 to initiate a third actuation cycle will cause the needle to again move in a distal direction, again causing the needle 60 to rotate ninety degrees into the position, as previously described.

By being able to reset the ferrule 112, 114 by squeezing the actuator lever 16 after taking a first stitch, the device can be called a "running-stitch" device, capable of making multiple suture stitches in vivo, through a minimally invasive access opening, without the need to remove the device and manually reset between stitches. This may be especially helpful in the replacement of chordae tendinae of a mitral valve leaflet, as a first stitch may be placed in a leaflet, the device reset, and then a second stitch placed in a papillary muscle. The second stitch may be secured after adjusting the length of the suture between the leaflet and the papillary muscle to a desired distance to reduce or eliminate leaflet prolapse.

FIGS. 4A-4C are side, enlarged and proximal views, respectively, of the surgical suturing device 10 of FIG. 1, shown in a ready to stitch or initial state. In particular, FIG. 4B illustrates an enlarged view of the tip assembly 26 of the surgical suturing device 10 showing a distal tip frame 88, ferrule holders 90 defined by the frame 88. A first suture 94 and a second suture 96 are each attached to a corresponding one of the ferrules 112, 114, which are not visible as they are releasably retained within the ferrule holders 90. Portions of the frame 88 define a notch, or a tissue bite area 92, which is configured to receive tissue to be sutured, such as a papillary muscle during a minimally invasive surgical procedure. Although needles 102 (illustrated in FIG. 5B) are not visible in this view, each of the needles 102 is in the first needle position and in a first rotational position prior to the initial actuation of the actuation lever 16 to initiate the first actuation cycle.

FIG. 4C illustrates a proximal view of a portion of the housing 12 of the surgical suturing device 10 focused on the indicator window portion 38 of the housing 12 which displays a light segment 44 (i.e., a first visual indication) of the device mode state indicator 40. In this embodiment a light segment indicates an initial state or ready to stitch state of the surgical suturing device 10, indicating that the first actuation cycle may be initiated. In other embodiments other indicating features may be displayed, such as a darker color, a character indicator—for example a number, letter or symbol, or a specific color unique to such an alternate embodiment.

FIGS. 5A-5C are side, enlarged and proximal views, respectively, of the surgical suturing device 10 of FIG. 1, after the first actuation cycle has been initiated, and the surgical suturing device 10 is illustrated in a partially actuated state and is transitioning to a ready to reset state. In particular, the actuation lever 16 has been squeezed in direction 98 towards the handle 14 of the surgical suturing device 10 by a user from the first actuator position towards the second actuator position.

As the actuation lever 16, is squeezed in direction 98 towards the handle 14 of the surgical suturing device 10, each of the pair of needles 102 extend distally in a direction 100 from the first needle position towards the second needle position, and one or both of the pair of needles 102 may be identical to the needle 60 previously described. In some embodiments, only a single needle 102 may be used, and in other embodiments, only a single needle 102 of the pair of needles 104 may be extended at a time. In other embodiments, more than two needles 102 may be used. Referring again to FIG. 5B, as the pair of needles 102 displace from the first needle position towards the second needle position, each of the needle tips 104 extend into and through the tissue bite area 92 in a linear path that is aligned with a corresponding one of the ferrules 112, 114. While the enlarged view in FIG. 5B is shown without tissue for purposes of clarity, if tissue is positioned within the tissue bite area 92 it would be pierced by the needles. FIG. 5C illustrates a proximal view of a portion of the housing 12 of the surgical suturing device 10 focused on the indicator window portion 38 of the housing 12. As the actuation lever 16 is squeezed, the biased cam pin 58 rides in the cam path 63 of the barrel 62 to rotate the barrel 62, as previously described, and thus each of the needles 102 rotates about the corresponding needle axis from the first rotational position towards a second rotational position, which may be 90 degrees offset from the first rotational position. Because the attached keyed extension 65 interfaces and is attached to the state indicator 40, the state indicator 40 also rotates along with the barrel 62. As these elements rotate in a clockwise direction, the state indicator 40 also rotates in a clockwise direction 106. The indicator window portion 38 of the housing 12 displays a portion of the light segment 44 of the device mode state indicator 40, as well as a portion of the advancing dark segment 42 (i.e., a second visual indication) of the device mode state indicator 40 during this rotation. In this embodiment, the cam barrel 62 and attached state indicator 40 rotate clockwise, but other embodiments may have similar features that rotate counterclockwise by virtue of the configuration of an alternate cam path in the cam barrel 62. Alternate embodiments may also have curved, flexible, or otherwise shaped or oriented needles as compared to the straight needles shown herein.

FIGS. 6A-6C are side, enlarged and proximal views, respectively, of the surgical suturing device of FIG. 1 in a ready to reset state. FIG. 6B illustrates an enlarged view of the tip assembly 26 of the surgical suturing device 10 showing the needles 102 in the second needle position in which the needle tips 104 engage a corresponding one of the ferrules 112, 114. In this embodiment, the actuation lever 16 has been fully displaced from the first actuator position to the second actuator position, and the needle 102 has been rotated into the second rotational position as the needle translated from the first needle position to the second needle position. As the actuation lever 16 is released, the needles 102 displace from the second needle position back to the first needle position, such that the needle tips 104 are retracted back through the tissue bite area 92 in proximal direction 108. Because the needles 102 are in the second rotational position, the ferrules 112, 114 are secured to the corresponding needle tips 104 and the attached first suture 94 and second suture 96 have been retracted proximally through the tissue bite area 92. While the enlarged view in FIG. 6B is shown without tissue for purposes of clarity, if tissue is positioned within the tissue bite area 92 it would be pierced by the needle tips 104, and the needle tips 104 would have brought the ferrules 112, 114 and attached suture 94, 96 back through the tissue as the needles 102 were retracted to the first needle position. In some embodiments, the needles 102 are in the second rotational position as each needle 102 reaches the second needle position from the first needle position, and the needle 102 remains in the second rotational position as the needle displaced distally from the second needle position to the first needle position to complete the first actuation cycle. However, in some embodiments, the needles 102 remain in the first rotational position as each needle reaches the second needle position from the first needle position, and each needle rotates from the first rotational position to the second rotational position as the needles 102 displace proximally from the second needle position to the first needle position (e.g., as the actuation lever 16 is released and displaced from the second actuator position to the first actuator position) to complete the first actuation cycle.

FIG. 6C illustrates a proximal view of a portion of the housing 12 of the surgical suturing device 10 focused on the indicator window portion 38 of the housing 12 after the completion of the first actuation cycle. The indicator window portion 38 of the housing 12 now displays only the dark segment 42 of the device mode state indicator 40. In this embodiment, the display of the dark segment 42 indicates that the surgical suturing device 10 has been actuated a single time (i.e., for a first actuation cycle) and is ready to be reset prior to being actuated to perform a subsequent stitching operation (i.e., a second actuation cycle).

FIGS. 7A-7C are side, enlarged and proximal views, respectively, of the surgical suturing device 10 of FIG. 1, shown in a partially actuated state, after the initiation of a second actuation cycle in which the device is transitioning to a ready to stitch or initial state. In this partially actuated state, the actuation lever 16 is squeezed once again in direction 110 towards the handle 14 of the surgical suturing device 10. FIG. 7B illustrates an enlarged view of the tip assembly 26 of the surgical suturing device 10 with the first ferrule 112 and first suture 94 engaged with one of the needle tips 104 and the second ferrule 114 and second suture 96 engaged with the other one of the needle tips 104. As the actuation lever 16, is squeezed in direction 110 towards the handle 14 of the surgical suturing device 10, the pair of needles 102 are extended distally in a direction 116 into and across the tissue bite area 92, where the needles 102 will return the ferrules 112, 114 to their respective ferrule holders 90 in the tip assembly 26 when the needles 102 extend to the second needle position. The enlarged view in FIG. 7B is shown without tissue for purposes of clarity, and in this step, the tip assembly 26 of the surgical suturing device 10 would be physically displaced away from the tissue to reset the ferrules 112, 114 and attached suture 94, 96 back into the ferrule holders 90.

FIG. 7C illustrates a proximal view of a portion of the housing 12 of the surgical suturing device 10 focused on the indicator window portion 38 of the housing 12. As the actuation lever 16 is squeezed, and as the needles 102 displace from the first needle position to the second needle position, the biased cam pin 58 rides in the cam path 63 of the barrel 62 to rotate the barrel 62, as previously described. Thus, when the needles extend into the second needle position, the needles are rotated about the needle axis from the second rotational position to a third rotational position, which may be 90 degrees offset from the second rotational position. When the needle tips 104 with the engaged ferrules 112, 114 extend into the second needle position and the needles are rotated into the third position, the ferrules 112, 114 may be engaged by a stripping element as previously described to retain the ferrules 112, 114 within the ferrule holders 90 as the needles 102 retract from the second needle position back to the first needle position to complete the second actuation cycle. In particular, a flat portion 111 (see FIG. 5B) at or adjacent to the needle tips 104 may be aligned with the stripping element that is disposed proximal to the ferrule holders 90 such that the proximal end edge of the ferrules 112, 114 may be engaged by the stripping element in this rotational position. However, in the rotational position in which the flat portion at or adjacent to the needle tips 104 is not aligned with the stripping element (i.e., disposed at a 90 degree angle with the stripping element), such as when the needle tips 104 engage and retain the ferrules 112, 114 when extending into the second needle position, the stripping element cannot engage the proximal end edge of the ferrules 112, 114 and the ferrules are secured to the needle tips 104 as the needles 102 are retracted from the second needle position to the first needle position.

In other embodiments, such as when the needles 102 rotate from the first rotational position to the second rotational position as the needles 102 displace proximally from the second needle position to the first needle position to complete the first actuation cycle, the needles 102 may remain in the second rotational position during the second actuation cycle as each needle 102 reaches the second needle position from the first needle position. In such an embodiment, each needle 102 then rotates from the second rotational position to the third rotational position as the needles 102 displace proximally from the second needle position to the first needle position (e.g., as the actuation lever 16 is released and displaced from the second actuator position to the first actuator position) to complete the second actuation cycle. The ferrules 112, 114 may be stripped as described above as the needles 102 begin to translate from the second needle position towards the first needle position during the second actuation cycle.

As the attached keyed extension 65 is coupled to the state indicator 40, the state indicator 40 also rotates along with the barrel 62. As these elements rotate in a clockwise direction, the state indicator 40 also rotates in a clockwise direction 118. The indicator window portion 38 of the housing 12 displays a portion of the dark segment 42 of the device mode state indicator 40, as well as a portion of the advancing light segment 44 (i.e., a third visual indication), or a further type of segment, of the device mode state indicator 40 during this rotation. At the completion of the second actuation cycle, the indicator window portion 38 of the housing 12 displays the advanced light segment 44. In this embodiment, the cam barrel 62 and attached state indicator 40 rotate clockwise, but other embodiments may have similar features that rotate counterclockwise by virtue of the configuration of an alternate cam path in the cam barrel 62. Alternate embodiments of such a device may have only a single needle or more than two needles. Alternate embodiments may also have curved, flexible, or otherwise shaped or oriented needles as compared to the straight needles shown herein. At the completion of the second actuation cycle, the surgical suturing device 10 is configured for a third actuation cycle, which may be identical or similar to the first actuation cycle.

FIGS. 8A-8F are a series of proximal schematic views of a suturing device indicator of the suturing device of FIG. 1.

FIGS. 8A-8F illustrate an embodiment of a device state indicator having twelve segments, alternating six first (e.g., light-colored) segments—L1, L2, L3, L4, L5, L6 with six second (e.g., dark-colored) segments—D1, D2, D3, D4, D5, D6. For the purpose of clarity of explanation, this device mode indicator is illustrated without a housing or any other device element that may interfere with a full view of the device state in the present embodiment. A viewable position 120 or viewable segment is indicated as the segment or portion of the device state indicator that would be visible to a user of the surgical suturing device 10. For further purposes of clarity, the indicator fin 22 position is also shown in FIGS. 8A-8F to demonstrate that when the rotational position of the rotation adapter 20 is rotated, that a segment having the same appearance, light or dark, remains or is displayed in the viewable position 120 regardless of the rotational position of the rotation adapter 20. FIGS. 8A-8D illustrate four successive 60-degree clockwise rotations of the rotation adapter 20 as shown by the position of the indicator fin 22. It should be noted that as the indicator fin 22 position advances clockwise 60 degrees in FIGS. 8B, 8C, and 8D, relative to a starting position in FIG. 8A, a dark segment is in the viewable position 120. For example, in FIG. 8A, dark segment D1 is in the viewable position 120. In FIG. 8B, dark segment D16 is in the viewable position 120 while the indicator fin 22 has advanced clockwise 60 degrees. In FIG. 8C, dark segment D5 is in the viewable position 120 while the indicator fin 22 has advanced clockwise 60 degrees. Finally, in FIG. 8D, dark segment D4 is in the viewable position 120 while the indicator fin 22 has advanced clockwise 60 degrees. This illustrates that the same device state indicator state—light or dark, in this embodiment—is reflected or displayed in the viewable position independent of which position the rotation adapter 20, as indicated by the position of the indicator fin 22 in each of FIG. 8A-8B. Direction 122, direction 124, direction 126, direction 128, and direction 130 indicate directions in which the of the rotation adapter 20 is rotated.

The following equation may be used to calculate the number of radial sectors (with reference to FIG. 8A):

$$RS = RP \times DS$$

where:
RP=Rotational positions available to device
DS=Device States
$\theta_{RS}$=Angle of Radial Sectors $$\theta_{RS} = \frac{360}{RS}$$

OR $$\theta_{RS} = \frac{360}{RP \times DS}$$

Example: Radial Sectors=(6 Rotational Positions)× (2 Device States)=12 θ sector=360/12=30°

Figure 9A:
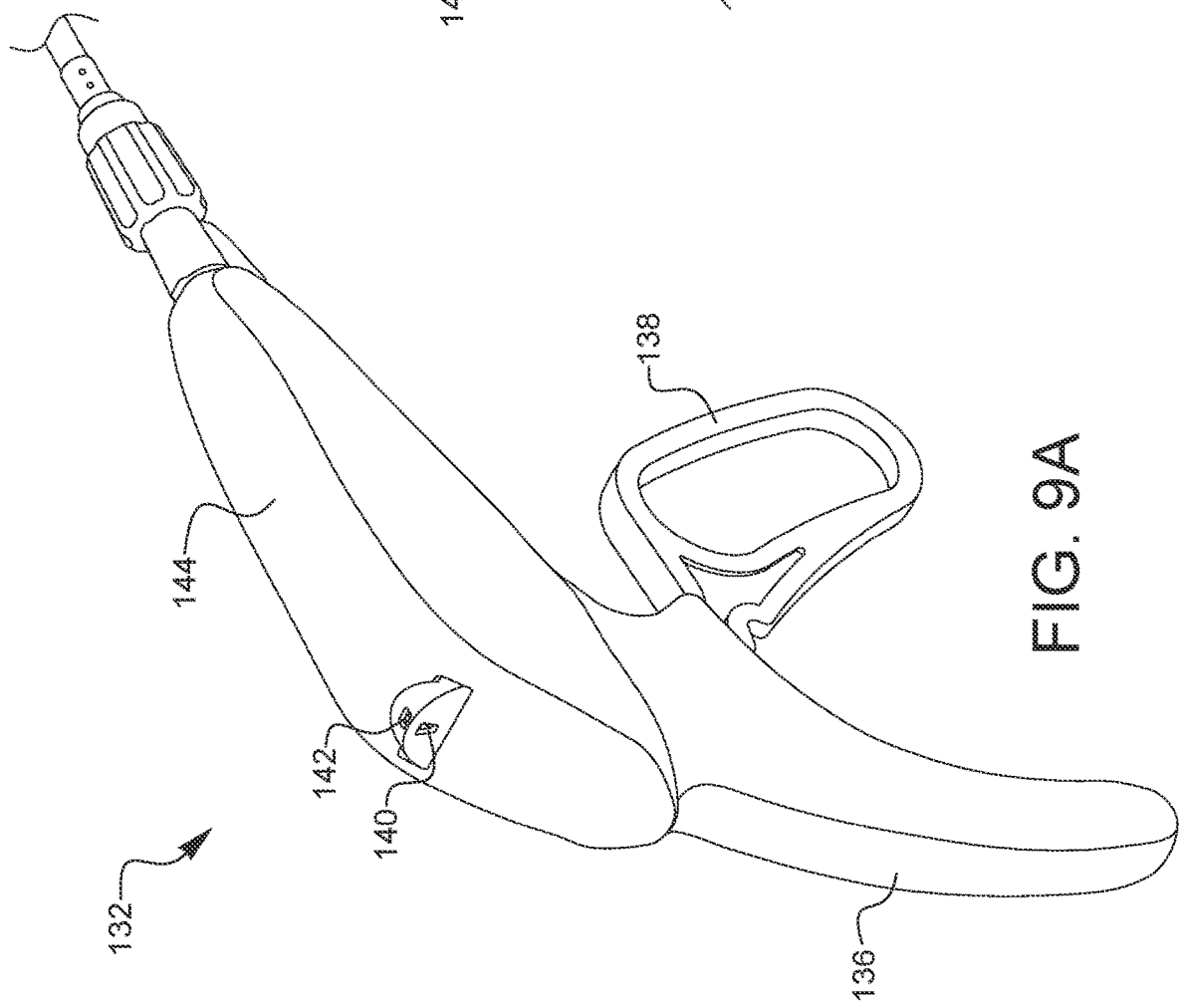
FIGS. 9A and 9B are top right proximal perspective and proximal views of another embodiment of a surgical suturing device.
Figure 9B:
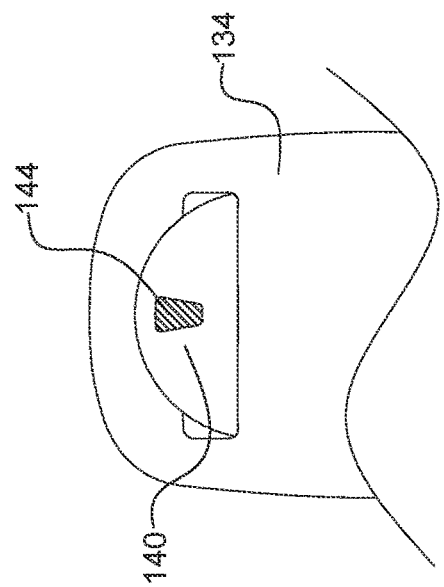

FIGS. 9A and 9B are top right proximal perspective and proximal views of another embodiment of a surgical suturing device 132 having a housing 134, a handle 136, and actuation lever 138, a proximal indicator window 140 and a top indicator window 142, which both indicate position or state associated with a dark segment 144.

Figure 10B:
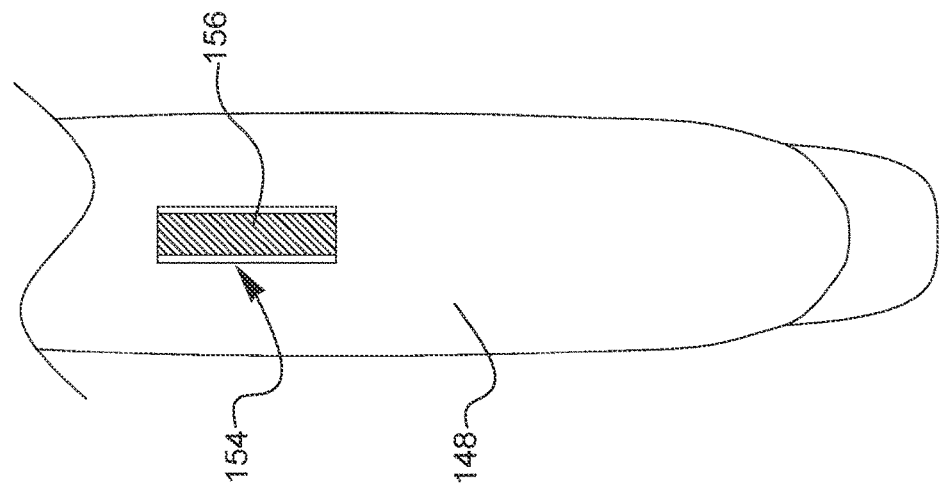
FIGS. 10A and 10B are top right proximal perspective and top views of another embodiment of a surgical suturing device.
Figure 10A:
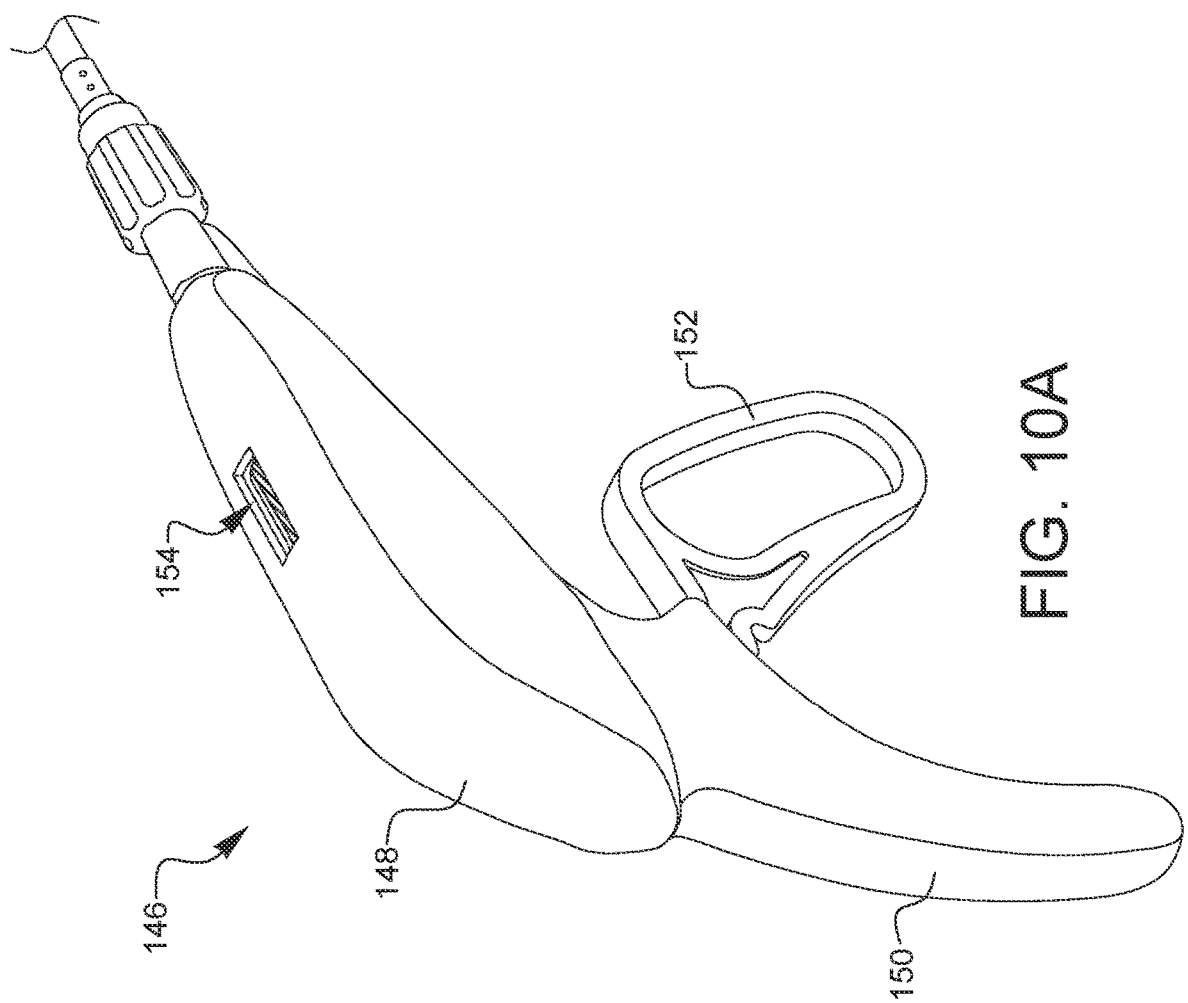

FIGS. 10A and 10B are top right proximal perspective and top views of another embodiment of a surgical suturing device 146 having a housing 148, a handle 150, an actuation lever 152, and a top indicator window 154 that indicates a dark segment 156. The rotation adaptor associated with the top indicator window 154 may be coupled to the needle in a similar or identical manner as that previously described.

FIGS. 11A-11F are a series of proximal schematic views of portions of alternate embodiments of surgical suturing devices that include a proximal indicator window 158. The device may include a housing 160 and an indicator mark 162, 164, 164, 166, 168, 170, and 172.

Various advantages of a suturing device state indicator have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suturing device for minimally invasive surgery, comprising:
   a housing;
   an actuator displaceably coupled to a first portion of the housing;
   a shaft extending from a proximal end to a distal end along a shaft axis, wherein the proximal end of the shaft is coupled to a second portion of the housing, wherein the shaft includes one or more interior surfaces defining an interior portion;
   a needle extending from a proximal end to a distal end about a needle axis, wherein a first portion of the needle is coupled to a portion of the actuator such that a displacement of the actuator displaces the needle from a first needle position to a second needle position, and wherein a needle tip is disposed at the distal end of the needle, the needle tip being configured to penetrate a portion of tissue to be sutured; and
   a state indicator coupled to a second portion of the needle, the state indicator being operable between a first state and a second state, wherein when the state indicator is in the first state, the state indicator provides a first visual indication, when the state indicator is in the second state, the state indicator provides a second visual indication, wherein the first visual indication is different than the second visual indication, and wherein:
      when the needle is in the first needle position and a first rotational position, the state indicator is in the first state providing the first visual indication,
      when as the needle translates between the first needle position and the second needle position in a first actuation cycle, (a) the needle rotates about the needle axis from the first rotational position towards a second rotational position, and (b) as the needle rotates about the needle axis from the first rotational position towards the second rotational position, the state indicator rotates between the first state and the second state, and
      after the needle has translated from the second needle position and into the first needle position at the completion of the first actuation cycle, the needle is in the second rotational position, and the state indicator is in the second state providing the second visual indication.

2. The suturing device of claim 1, wherein:
   the needle rotates about the needle axis from the first rotational position to the second rotational position as the needle translates from the first needle position to the second needle position during the first actuation cycle.

3. The suturing device of claim 2, wherein:
   the needle does not rotate about the needle axis as the needle translates from the second needle position to the first needle position during the first actuation cycle.

4. The suturing device of claim 2, wherein when the needle translates to the second needle position during the first actuation cycle, the needle tip is configured to engage a ferrule that is coupled to a portion of suture, and when the needle translates from the second needle position to the first needle position during the first actuation cycle, the needle tip is configured to be secured to the ferrule.

5. The suturing device of claim 4, wherein when the needle translates from the first needle position to the second needle position during the second actuation cycle, the needle tip is configured to be secured to the ferrule, and as the needle begins to translate from the second needle position to the first needle position during the second actuation cycle, the ferrule is configured to be removed from the needle tip.

6. The suturing device of claim 1, wherein:
   the needle rotates about the needle axis from the first rotational position to the second rotational position as the needle translates from the second needle position to the first needle position during the first actuation cycle.

7. The suturing device of claim 6, wherein:
   the needle does not rotate about the needle axis as the needle translates from the first needle position to the second needle position during the first actuation cycle.

8. The suturing device of claim 7, wherein the first visual indication is the same as the third visual indication.

9. The suturing device of claim 1, wherein the state indicator is operable between the first state, the second state, and a third state, wherein when the state indicator is in the third state, the state indicator provides a third visual indication, wherein the second visual indication is different that the third visual indication, and wherein:
   after the needle is in the second rotational position following the completion of the first actuation cycle, and when the needle translates between the first needle position and the second needle position in a second actuation cycle, (a) the needle rotates about the needle axis from the second rotational position towards a third rotational position, and (b) as the needle rotates about the needle axis from the second rotational position towards the third rotational position, the state indicator rotates between the second state and the third state, and
   after the needle has translated from the second needle position and into the first needle position at the completion of the second actuation cycle, the needle is in the third rotational position, and the state indicator is in the third state providing the third visual indication.

10. The suturing device of claim 9, wherein:
    the needle rotates about the needle axis from the second rotational position to the third rotational position as the needle translates from the second needle position to the first needle position during the second actuation cycle.

11. The suturing device of claim 9, wherein:
the needle rotates about the needle axis from the second rotational position to the third rotational position as the needle translates from the first needle position to the second needle position during the second actuation cycle.

12. The suturing device of claim 1, wherein the actuator is displaceable between a first actuator position and a second actuator position, and when the actuator is displaced from the first actuator position to the second actuator position, the needle is translated linearly from the first needle position to the second needle position.

13. The suturing device of claim 1, wherein the state indicator is directly coupled to second portion of the needle such that as the needle rotates about the shaft axis, the state indicator rotates with the needle about the shaft axis.

14. The suturing device of claim 13, wherein the state indicator is slidably coupled to the second portion of the needle such that as the as the needle and the state indicator rotate about the shaft axis, the needle is displaceable relative to the state indicator along the needle axis as the needle translates between the first needle position and the second needle position.

15. The suturing device of claim 1, wherein the shaft is rotatably coupled to the second portion of the housing such that the shaft is configured to rotate about the shaft axis relative to the housing.

16. The suturing device of claim 15, wherein the shaft is configured to rotate from a first rotational increment to a second rotational increment, wherein the first rotational increment is separated from the second rotational increment by a radial distance of between 10 degrees and 90 degrees.

17. The suturing device of claim 16, wherein when the shaft is rotated from the first rotational increment to the second rotational increment, the state indicator displaces from the first visual indication to a third visual indication that is identical to the first visual indication.

18. The suturing device of claim 1, further comprising a tip assembly disposed at a distal end of the shaft, the tip assembly including a frame in which one or more portions define a tissue bite area, and wherein a ferrule holder is disposed at a portion of the frame that is disposed at a distal end of the tissue bite area and that is linearly aligned with the needle axis such that when the needle is in the second needle position, the needle tip is configured to engage a ferrule releasably disposed within the ferrule holder, and wherein the tissue bite area is configured to receive a portion of tissue to be sutured.

19. The suturing device of claim 18, wherein the shaft is rotatably coupled to the second portion of the housing such that the shaft is configured to rotate about the shaft axis relative to the housing, and wherein the frame of the tip assembly is fixedly secured to the distal end of the shaft such that the tip assembly rotates with the shaft.

20. The suturing device of claim 1, wherein a third portion of the needle is disposed within the interior portion of the shaft.

* * * * *